(12) United States Patent
Calderon et al.

(10) Patent No.: US 7,242,742 B2
(45) Date of Patent: Jul. 10, 2007

(54) MEGAVOLTAGE IMAGING SYSTEM

(75) Inventors: Edward Lewis Calderon, Pittsburg, CA (US); Francisco M. Hernandez-Guerra, Concord, CA (US); Ali Bani-Hashemi, Walnut Creek, CA (US); Farhad A. Ghelmansarai, Danville, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 70 days.

(21) Appl. No.: 11/187,128

(22) Filed: Jul. 21, 2005

(65) Prior Publication Data

US 2007/0018111 A1 Jan. 25, 2007

(51) Int. Cl.
*A61N 5/10* (2006.01)
*A61B 5/05* (2006.01)

(52) U.S. Cl. .................... 378/65; 378/64; 378/87; 378/145; 600/415; 600/411; 600/410

(58) Field of Classification Search ............ 378/65, 378/64, 87, 98, 145, 165; 600/415, 411, 600/410, 407, 425
See application file for complete search history.

(56) References Cited

U.S. PATENT DOCUMENTS

| | | | | |
|---|---|---|---|---|
| 5,621,779 | A | * | 4/1997 | Hughes et al. ............... 378/65 |
| 6,445,766 | B1 | * | 9/2002 | Whitham .................... 378/65 |
| 6,459,762 | B1 | * | 10/2002 | Wong et al. ................. 378/65 |

* cited by examiner

*Primary Examiner*—Tuyet Thi Vo

(57) ABSTRACT

Some embodiments include a particle source, an RF power source, an accelerator waveguide, and an imaging device. The particle source is to generate a first injector current and a second injector current, the first injector current being less than the second injector current. The RF power source is to generate first RF power at a first pulse rate and second RF power at a second pulse rate, the first pulse rate being greater than the second pulse rate. The accelerator waveguide is to accelerate a first electron beam based on the first injector current and the first RF power and to accelerate a second electron beam based on the second injector current and the second RF power, and the imaging device is to acquire an image based on the first electron beam. The second electron beam may be used to deliver treatment radiation to a patient.

8 Claims, 8 Drawing Sheets

MEGAVOLTAGE IMAGING SYSTEM

BACKGROUND

1. Field

The embodiments described herein relate generally to particle accelerators. More particularly, the described embodiments relate to particle accelerators used for treatment and/or imaging.

2. Description

A particle accelerator produces charged particles having particular energies. In one common application, a particle accelerator produces a radiation beam used for medical radiation treatment. The beam may be directed toward a target area of a patient in order to destroy cells within the target area by causing ionizations within the cells or other radiation-induced cell damage.

A conventional particle accelerator includes a particle source, an accelerator waveguide, an RF (radio-frequency) power source, and a bending magnet. The particle source may comprise an electron gun that generates and transmits electrons to the waveguide. The RF power source, which may comprise a magnetron or a klystron/RF driver, delivers an electromagnetic wave to a window built into the waveguide. The electromagnetic wave enters the waveguide through the window and oscillates within the waveguide. The oscillations accelerate the transmitted electrons through the waveguide. Finally, the bending magnet receives the accelerated electrons, filters them according to their energies, and emits them toward a target area.

Radiation treatment plans are designed to maximize radiation delivered to a target while minimizing radiation delivered to healthy tissue. However, designers of a treatment plan assume that relevant portions of a patient will be in a particular position relative to a particle accelerator during delivery of the treatment radiation. If the relevant portions are not positioned exactly as required by the treatment plan, the goals of maximizing target radiation and minimizing healthy tissue radiation may not be achieved. More specifically, errors in positioning the patient can cause the delivery of low radiation doses to tumors and high radiation doses to sensitive healthy tissue. The potential for misdelivery increases with increased positioning errors.

Conventional imaging systems may be used to determine a patient position prior to treatment according to a particular radiation treatment plan. For example, a radiation beam is emitted by a particle accelerator, passes through a volume of the patient and is received by an imaging system. The imaging system generates a two-dimensional portal image of the patient volume, which can be used to determine whether the patient is in a position dictated by the particular treatment plan.

A radiation beam used for imaging as described above delivers a radiation dose to the patient volume. The dose is preferably significantly less than a dose rate used for radiation treatment, but suitable to produce a satisfactory portal image. Low dose rates are particularly desirable if cone beam imaging is used to produce a three-dimensional image of the patient, since such imaging requires the acquisition of several two-dimensional portal images.

Conventional particle accelerators are unable to efficiently generate a radiation beam that provides a dose rate suitable for imaging at a given energy. Attempts have been made to output a radiation beam during beam formation for imaging purposes. These attempts are based on the low dose rates provided by a radiation beam while the beam is formed within an accelerator waveguide. For example, dose rates may be sufficiently low for imaging during a period while a beam forms within an accelerator waveguide. However, the dose rate over time is unstable and non-linear during the beam formation period. These characteristics are caused at least in part by beam loading and thermal deformation of the accelerator waveguide, both of which unpredictably change the resonant frequency of the waveguide during beam formation. Generation of a low-dose radiation beam can therefore be both difficult and unpredictable.

SUMMARY

In order to address the foregoing, some embodiments provide a system, method, apparatus, and means to control a particle source to generate a first injector current, control an RF power source to generate first RF power at a first pulse rate, generate a first electron beam based on the first injector current and the first RF power, and acquire an image based on the first electron beam. Embodiments may further provide control of the particle source to generate a second injector current, control of the RF power source to generate second RF power at a second pulse rate, generation of a second electron beam based on the second injector current and the second RF power, and delivery of treatment radiation to a patient using the second electron beam. The first injector current may be less than the second injector current, and the first pulse rate may be greater than the second pulse rate.

Further to the foregoing aspect, some embodiments include selection of electrons of the first electron beam having a first selected energy, and selection of electrons of the second electron beam having a second selected energy, wherein the first selected energy is substantially equal to the second selected energy. An energy spectrum of the selected electrons of the first electron beam may be different from an energy spectrum of the selected electrons of the second electron beam.

Some embodiments provide a particle source, an RF power source, an accelerator waveguide, and an imaging device. The particle source is to generate a first injector current and a second injector current, the first injector current being less than the second injector current. The RF power source is to generate first RF power at a first pulse rate and second RF power at a second pulse rate, the first pulse rate being greater than the second pulse rate. The accelerator waveguide is to accelerate a first electron beam based on the first injector current and the first RF power and to accelerate a second electron beam based on the second injector current and the second RF power, and the imaging device is to acquire an image based on the first electron beam. The second electron beam may be used to deliver treatment radiation to a patient.

In a further aspect, also provided may be a bending envelope to select electrons of the first electron beam having a first selected energy, and to select electrons of the second electron beam having a second selected energy that is substantially equal to the first selected energy. An energy spectrum of the selected electrons of the first electron beam may be different from an energy spectrum of the selected electrons of the second electron beam.

The appended claims are not limited to the disclosed embodiments, however, as those in the art can readily adapt the descriptions herein to create other embodiments and applications.

BRIEF DESCRIPTION OF THE DRAWINGS

Embodiments will become readily apparent from consideration of the following specification as illustrated in the accompanying drawings, in which like reference numerals designate like parts, and wherein.

DETAILED DESCRIPTION

The following description is provided to enable a person in the art to make and use some embodiments and sets forth the best mode contemplated by the inventors for carrying out some embodiments. Various modifications, however, will remain readily apparent to those in the art.

Figure 1:
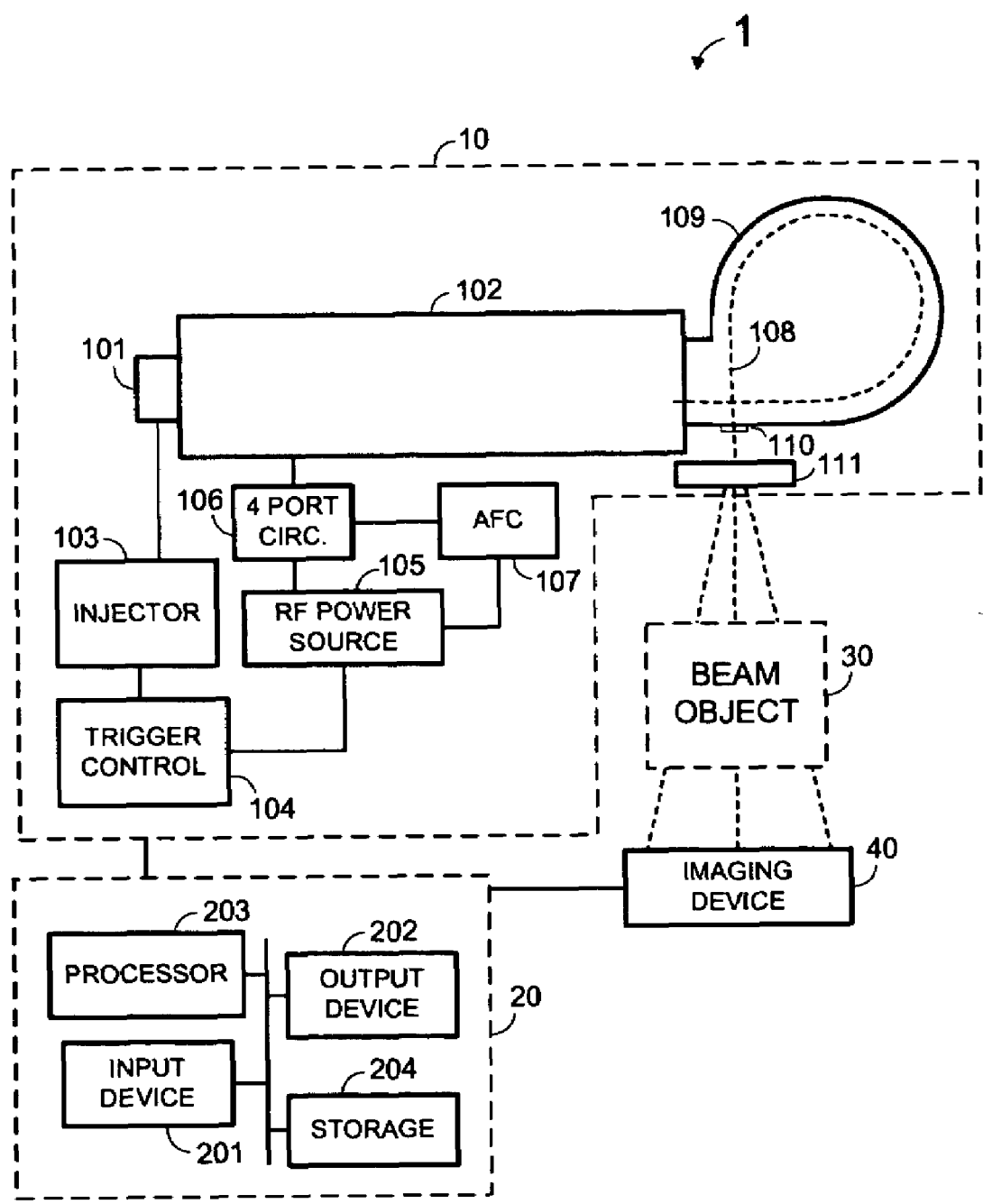
FIG. 1 is a block diagram of a linear accelerator system according to some embodiments.

FIG. 1 is a block diagram of system 1 according to some embodiments. System 1 includes particle accelerator 10, operator console 20, beam object 30 and imaging device 40. System 1 may be used to generate X-rays for use for imaging and/or for medical radiation treatment. System 1 may be employed in other applications according to some embodiments.

In one example according to some embodiments, system 1 operates to control a particle source to generate a first injector current, to control an RF power source to generate first RF power at a first pulse rate, to generate a first electron beam based on the first injector current and the first RF power, and to acquire an image based on the first electron beam. Also provided may be control of the particle source to generate a second injector current, control of the RF power source to generate second RF power at a second pulse rate, generation of a second electron beam based on the second injector current and the second RF power, and delivery of treatment radiation to a patient using the second electron beam. The first injector current may be less than the second injector current, and the first pulse rate may be greater than the second pulse rate. Some embodiments of the foregoing may provide more efficient imaging than prior systems.

Turning to the individual elements, particle accelerator 10 may output particles toward beam object 30 in response to commands received from operator console 20. Particle accelerator 10 includes particle source 101 for injecting particles such as electrons into accelerator waveguide 102. Particle source 101 may comprise an electron gun. Such an electron gun may include a heater, a cathode (thermionic or other type), a control grid (or diode gun), a focus electrode, an anode, and other elements. An injector current of particle source 101 may be controlled by injector pulses received from injector 103. Injector 103 may, in turn, receive trigger signals from trigger control 104 and generate the aforementioned injector pulses based thereon.

Accelerator waveguide 102 includes cavities that are designed and fabricated so that electric currents flowing on their surfaces generate electric fields that are suitable to accelerate the electrons. The oscillation of these electric fields within each cavity is delayed with respect to an upstream cavity so that an electron is further accelerated as it arrives at each cavity.

Accelerator waveguide 102 may include a "buncher" section of cavities to bunch the electrons and a second section of cavities to accelerate the bunched electrons. Some embodiments of particle accelerator 10 may include a pre-buncher for receiving particles from particle source 101 and for bunching the electrons before the electrons are received by accelerator waveguide 102.

The oscillating electric fields within the cavities of accelerator waveguide 102 are produced in part by an oscillating electromagnetic wave received by accelerator waveguide 102 from RF power source 105. Trigger control 104 may control RF power source 105 to generate an electromagnetic wave having a selected power and/or pulse rate. RF power source 105 may comprise any suitable currently- or hereafter-known pulsed power source. In some embodiments, RF power source 105 comprises a magnetron. RF power source 105 comprises a klystron and an RF driver in some embodiments.

Four port circulator 106 receives the electromagnetic wave before it is received by accelerator waveguide 102. Four port circulator 106 allows the electromagnetic wave to travel to accelerator waveguide 102 and prevents reflected power from returning to RF power source 105. Any reflected power is instead transmitted to automatic frequency control (AFC) 107.

AFC 107 receives the reflected power and transmits a signal to RF power source 105 based thereon. RF power source 105 controls the frequency of the electromagnetic wave based on the signal. Such control is intended to substantially eliminate the reflected power and to therefore obtain standing waves within accelerator waveguide 102. The frequency required to obtain standing waves is determined by the geometry of the accelerator waveguide, which may be affected by variations in temperature and by the number of electrons present in the electron beam within waveguide 102 (i.e., the "beam loading"). In this regard, the variations in temperature may cause mechanical deformation of waveguide 102 and the impedance inside waveguide 102 may change according to the beam loading.

Variations in temperature and beam loading are typically most pronounced while the electron beam is ramping up to full power and full dosage. An example of the foregoing will be described below with respect to FIG. 8.

Accelerator waveguide 102 may output beam 108 to bending envelope 109. Beam 108 includes a stream of electron bunches having various energies and bending envelope 109 may comprise an evacuated magnet to bend beam 108 two hundred seventy degrees. Bending envelope 109 may also focus beam 108 and select one or more energies for output.

Bending envelope 109 may select an energy by establishing a magnetic field that will allow only electrons of a selected energy (or of a range of energies surrounding the selected energy) to turn two hundred seventy degrees and exit through window 110. Other bending angles and/or systems to select energies may be used.

Window 110 may comprise two metal foils with water flowing therebetween for cooling. After passing through window 110, beam 108 passes through beam processing elements 111. Beam processing elements 111 may include one or more of scattering foils, shield blocks, dosimetry chambers, flattening filters, and collimator plates as are known in the art. Beam 108 is then received by beam object 30, which may comprise a patient, a target for generating X-rays, or another object.

Imaging device 40 receives beam 108 after passing through beam object 40. Imaging device 40 may comprise any system to acquire an image based on received X-rays and/or electrons. Imaging device 40 acquires images that are used before, during and after radiation treatment. For example, imaging device 40 may be used to acquire images for diagnosis, verification and recordation of a patient position, and verification and recordation of an internal patient portal to which treatment radiation is delivered. As described above, the effectiveness of radiation treatment often depends on the quality of the acquired images. Imaging device 40 may comprise a flat-panel device that converts received X-rays to light with a scintillator and that detects the light using charge-coupled devices.

Operator console 20 may control an injector current produced by particle source 101, and/or an amount of power generated by RF power source 105. Such control may include control of trigger control 104 to control injector 103 or RF power source 105, respectively. Operator console 20 may also control imaging device 40 to acquire an image.

Operator console 20 includes input device 201 for receiving instructions from an operator and output device 202, which may be a monitor for presenting operational parameters and/or a control interface of particle accelerator 10. Output device 202 may also present images acquired by imaging device 40 to verify patient positioning prior to radiation treatment.

Processor 203 executes program code according to some embodiments. The program code may be executable to control system 1 to operate as described herein. The program code may be stored in storage 204, which may comprise one or more storage media of identical or different types, including but not limited to a fixed disk, a floppy disk, a CD-ROM, a DVD-ROM, a Zip™ disk, a magnetic tape, and a signal. Storage 204 may, for example, store a software application to provide radiation treatment, radiation treatment plans, portal images, and other data used to perform radiation treatment. The other data mentioned above may include sets of hard-coded parameters for various elements of system 1, or "soft pots", that are associated with various functions of system 1. For example, one set of soft pots may be associated with imaging, while another set of soft pots may be associated with the delivery of treatment radiation.

Figure 2:
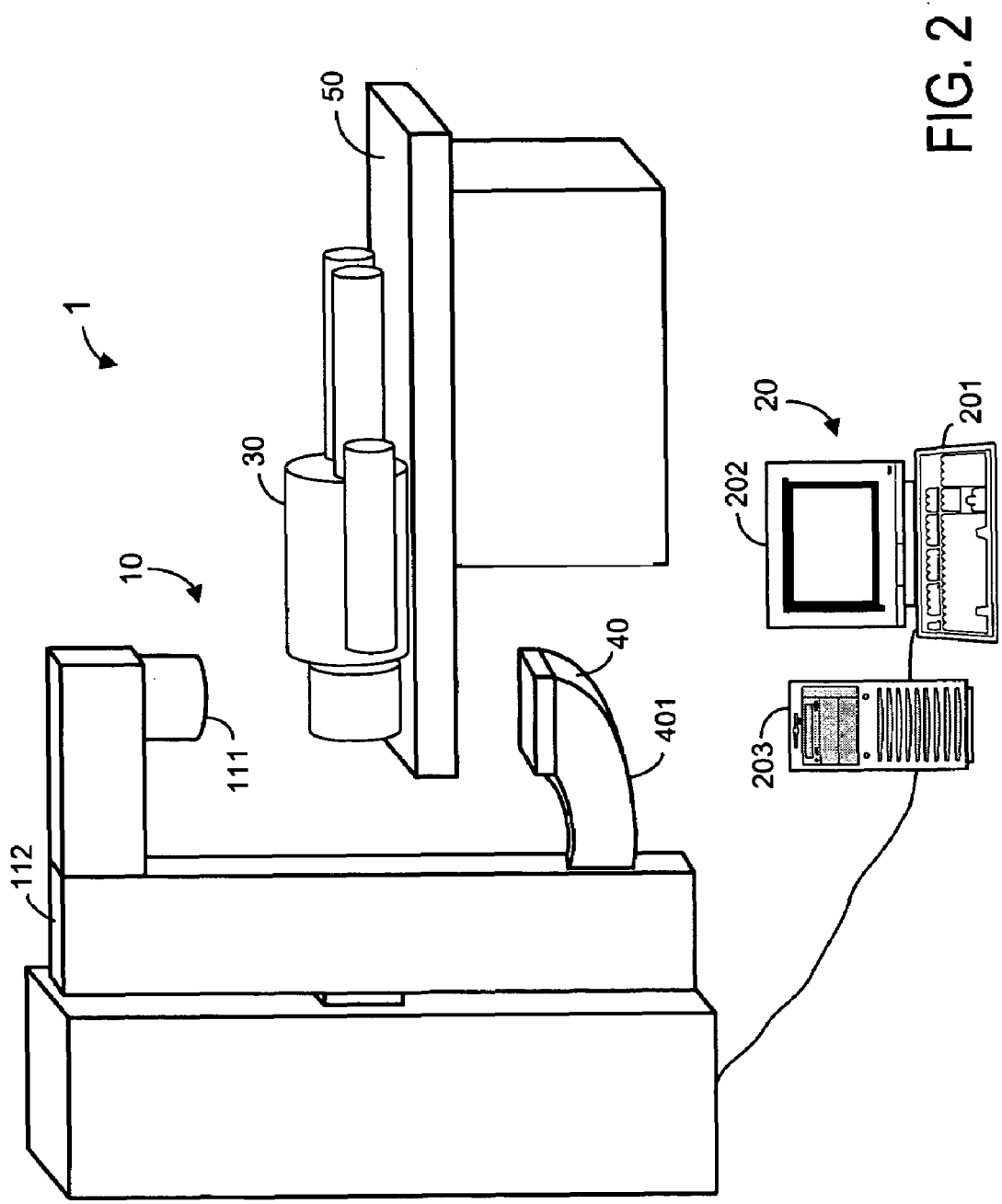
FIG. 2 is a perspective view of a linear accelerator system according to some embodiments.

FIG. 2 is a perspective view of system 1 according to some embodiments. Shown are particle accelerator 10, operator console 20, beam object 30, imaging device 40 and table 50. Beam object 30 comprises a patient positioned to receive treatment radiation according to a radiation treatment plan.

Particle accelerator 10 delivers beam 108 toward a volume of object 30 that is located at an isocenter of accelerator 10. Gantry 112 is rotatable around an axis before, during and after emission of beam 108. Rotation of gantry 112 may cause beam processing elements 111 and imaging device 40 to rotate around the isocenter such that the isocenter remains located between beam processing elements 111 and imaging device 40 during the rotation.

In some embodiments, imaging device 40 is a flat-panel imaging device using a scintillator layer and solid-state amorphous silicon photodiodes deployed in a two-dimensional array. The RID1640, offered by Perkin-Elmer®, Inc. of Fremont, Calif., is one suitable device. Imaging device 40 may be attached to gantry 112 in any manner, including via extendible and retractable housing 401.

Imaging device 40 may comprise other types of imaging devices. For example, X-ray radiation may also be converted to and stored as electrical charge without use of a scintillator layer. In such imaging devices, X-rays are absorbed directly by an array of amorphous selenium photoconductors. The photoconductors convert the X-rays directly to stored electrical charge that comprises an acquired image of a radiation field. Imaging device 40 may also comprise a CCD or tube-based camera. Such an imaging device may include a light-proof housing within which are disposed a scintillator, a mirror, and a camera.

Table 50 supports object 30 during radiation therapy. Table 50 is adjustable to ensure, along with rotation of gantry 112, that a volume of interest is positioned between elements 111 and imaging device 40. Table 50 may also be used to support devices used for acquisition of correction images, other calibration tasks and/or beam verification.

Operator console 20 may be located apart from particle accelerator 10, such as in a different room, in order to protect its operator from radiation. For example, accelerator 10 may be located in a heavily shielded room, such as a concrete vault, which shields the operator from radiation generated by accelerator 10.

Each of the devices shown in FIG. 2 may include less or more elements than those shown. In addition, embodiments are not limited to the devices shown in FIG. 2.

Figure 3:
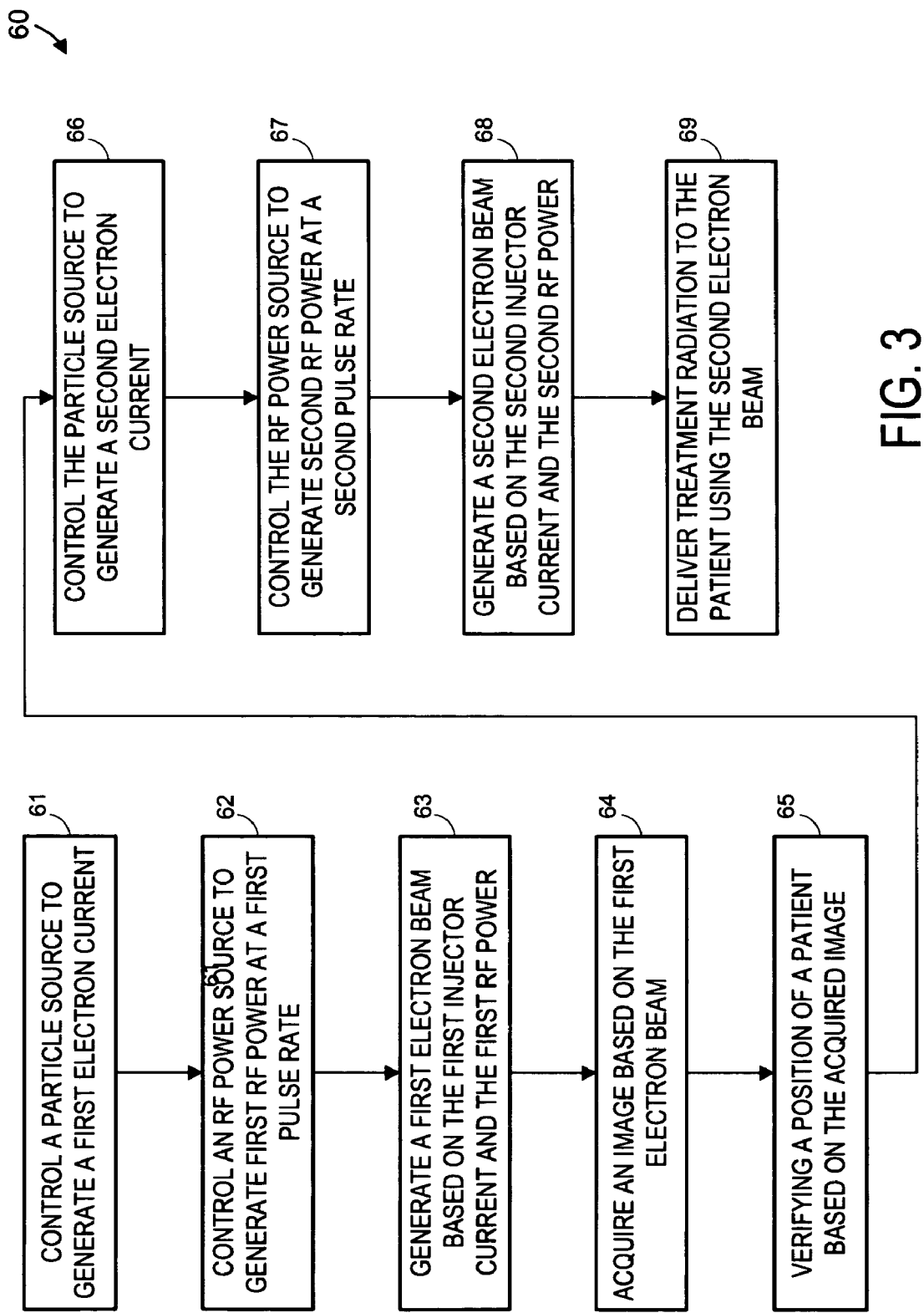
FIG. 3 is a flow diagram of process steps pursuant to some embodiments.

FIG. 3 is a flow diagram of process steps 60 according to some embodiments. Process steps 60 may be executed by one or more elements of particle accelerator 10, operator console 20, imaging device 40 and other devices. Accordingly, process steps 60 may be embodied in hardware and/or software. Process steps 60 will be described below with respect to the above-described elements, however it will be understood that process steps 60 may be implemented and executed differently than as described below.

Prior to step 61, an operator may use input device 201 of operator console 20 to input a command to begin radiation treatment. In response, processor 203 executes program code to execute a treatment plan stored in storage 204. The treatment plan may initially call for acquisition of an image of a patient to whom treatment radiation is to be delivered.

Therefore, at step 61, a particle source is controlled to generate a first electron current. For example, trigger control 104 may be controlled by operator console 20 to issue trigger signals to injector 103. Injector 103 then transmits injector pulses to particle source 101 based on the trigger signals. The injector pulses cause particle source 101 to generate a first electron current.

The first electron current may be an electron current suitable for imaging. The trigger signals, injector pulses and/or first electron current may be specified by soft pots stored in storage 204. These soft pots may be associated with imaging functions.

Next, at step 62, an RF power source is controlled to generate first RF power at a first pulse rate. According to some examples of step 62, RF power source 105 is controlled by trigger control 104 based on commands received from operator console 20. The first RF power and first pulse rate may be specified by program code, soft pots, or other elements of system 1, and/or may be suitable for imaging.

Figure 4:
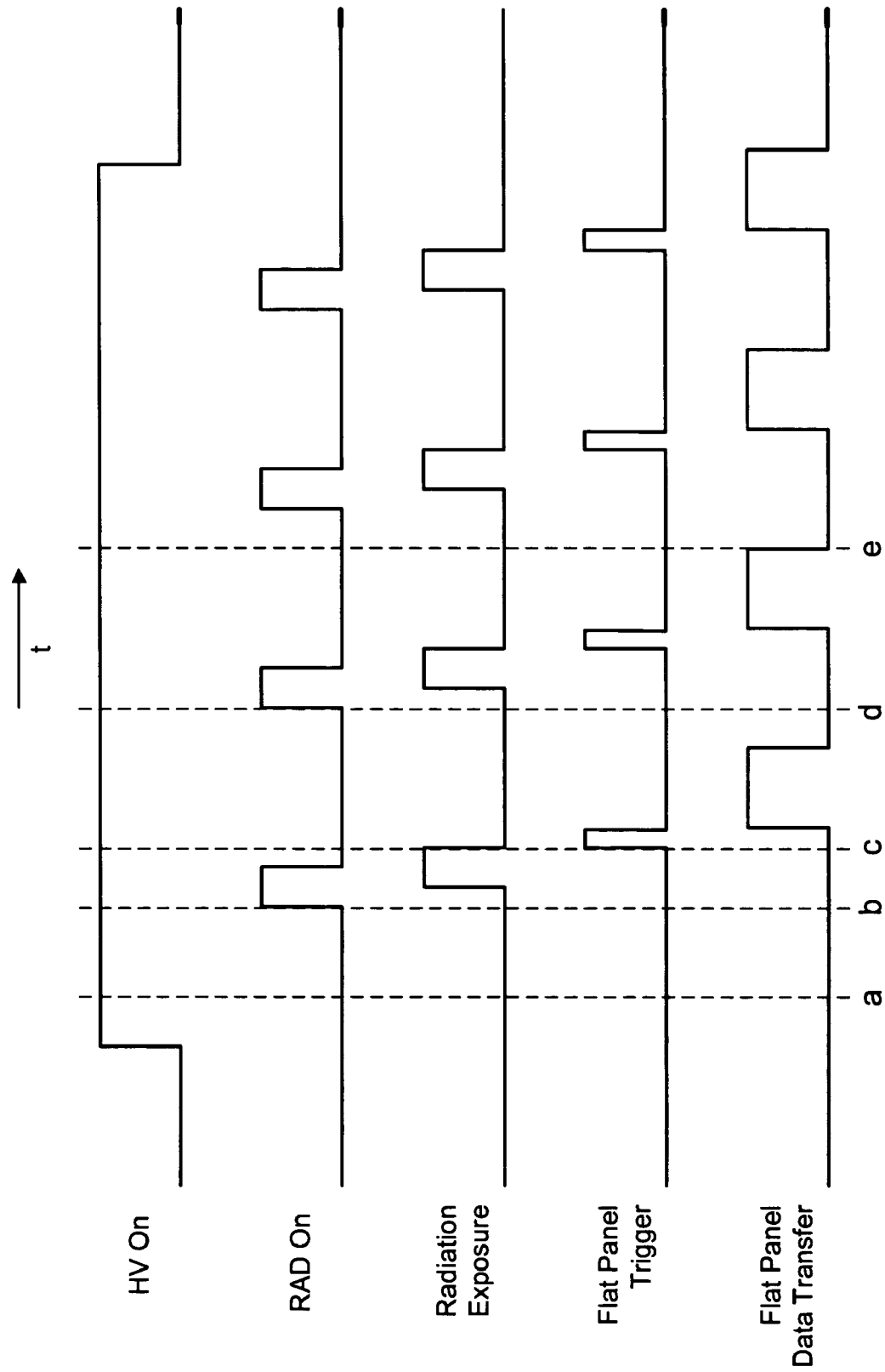
FIG. 4 is a waveform timing diagram according to some embodiments.

A first electron beam is generated based on the first injector current and the first RF power at step 63. FIG. 4 is a timing diagram illustrating signals used to generate the first electron beam according to some embodiments. It will be assumed that particle source 101 is generating the first electron current and that RF power source 105 is transmitting an electromagnetic wave to accelerator waveguide 102 at time a.

At time a, the active HV On signal causes RF power source 105 to transmit the electromagnetic wave to accelerator waveguide 102. The first electron beam is not generated at time a because the electromagnetic wave is not in phase with the injector current in a manner that will generate an accelerated electron beam as described above. Generation of the electron beam at step 63 begins at time b in response to the active RAD On signal.

The active Rad On signal causes the phase of the injector current to match the phase of the electromagnetic wave, which in turn causes generation of the first electron beam. Accordingly, and as shown by the Radiation Exposure waveform, object 30 receives radiation from the first electron beam a short time after the Rad On signal goes active. Object 30 continues to receive radiation from the first electron beam until a short time after the Rad On signal goes low, at which point the phase of the injector current changes again and thereby disables the first electron beam.

In some examples, imaging device 40 absorbs radiation during the active period of the Radiation Exposure waveform. The absorbed radiation consists of radiation that has been attenuated by structures of object 30 through which it has passed. Accordingly, the absorbed radiation may be used to create an image that spatially distinguishes these structures from one another based on their transparency to radiation.

Such an image may be acquired based on the first electron beam at step 64. More particularly, Flat Panel Trigger signal is activated at time c, causing imaging device 40 to transfer information to console 20. The information represents amounts of radiation absorbed at different locations of imaging device 40.

The foregoing sequence begins again at time d according to some embodiments, with a second image being acquired based on the first electron beam by time e. The second image may be acquired after moving gantry 112 to a rotational position different from its position during time b through time c. That is, gantry 112 may be rotated between time c and time d. The second image may therefore be acquired at a projection angle different from that at which the first image was acquired.

Processor 203 may generate a three-dimensional image based on the first image and the second image using currently- or hereafter-known image processing techniques. Such a three-dimensional image may also be based on other images of object 30 acquired at different rotational positions of gantry 112. According to some embodiments, at least 200 images are acquired at step 64.

Prior to acquisition of the image at step 64, some embodiments include selection of electrons of the first electron beam having a first selected energy. The electrons may be selected by controlling bending envelope 109 as is known in the art to select electrons of the selected energy. Such control typically results in the emission from window 110 of electrons having an energy spectrum that includes the selected energy.

Figure 5:
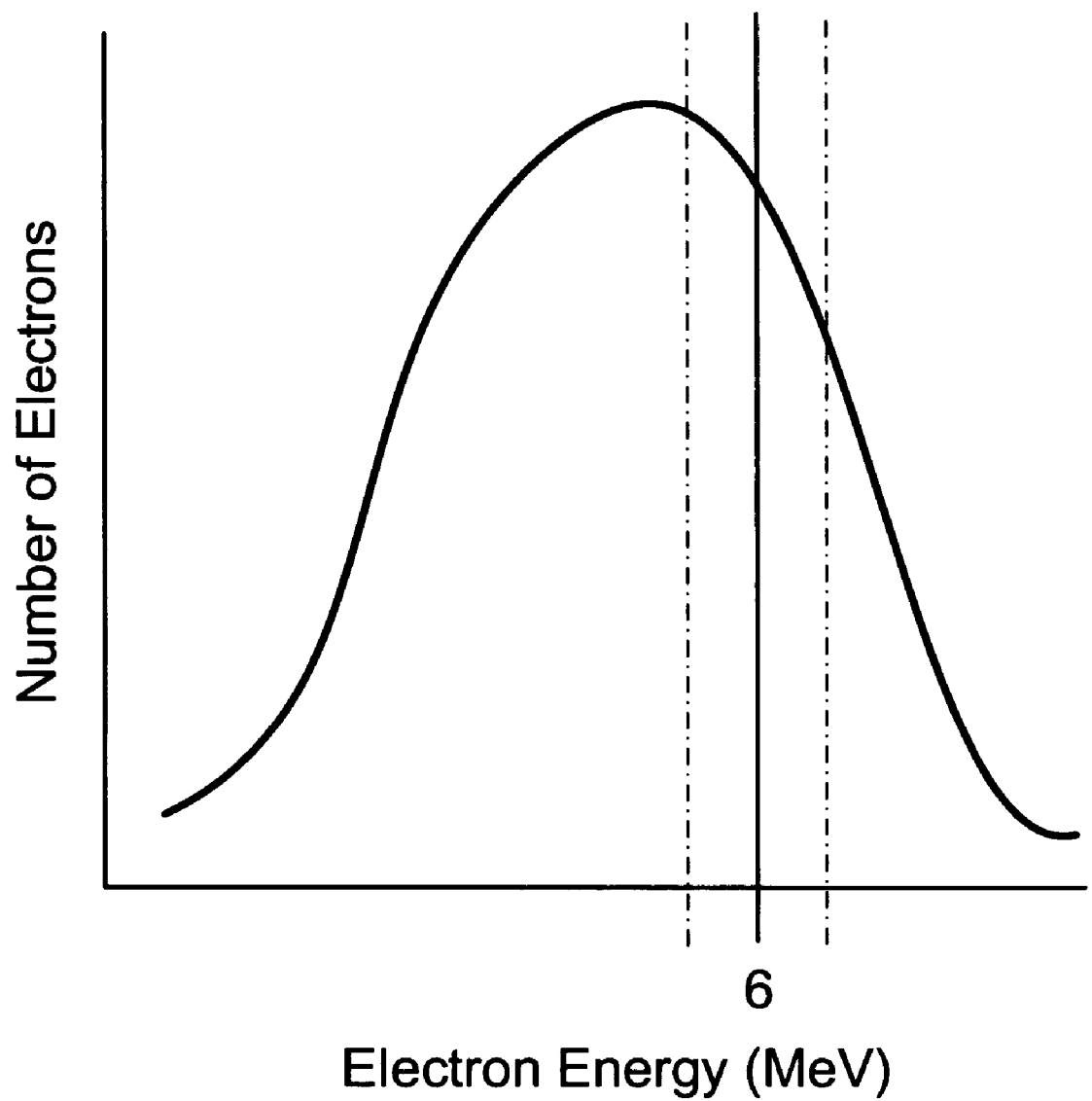
FIG. 5 is a graph of an energy spectrum associated with an electron beam generated according to some embodiments.

FIG. 5 illustrates an energy spectrum of the first electron beam according to some embodiments. The FIG. 5 example also shows a selected electron energy of 6 MeV, which results in the emission of electrons having energies falling between the dashed lines. The energy spectrum bounded by the dashed lines may be particularly suited to imaging according to some embodiments.

The foregoing example specifies a selected energy of 6 MeV. For purposes of example, the first electron current, first RF power, and first pulse rate may be 350 mA, 2 MW, and 250 pulses per second according to some embodiments. Other values for each of these parameters may be used according to some embodiments.

Figure 6:
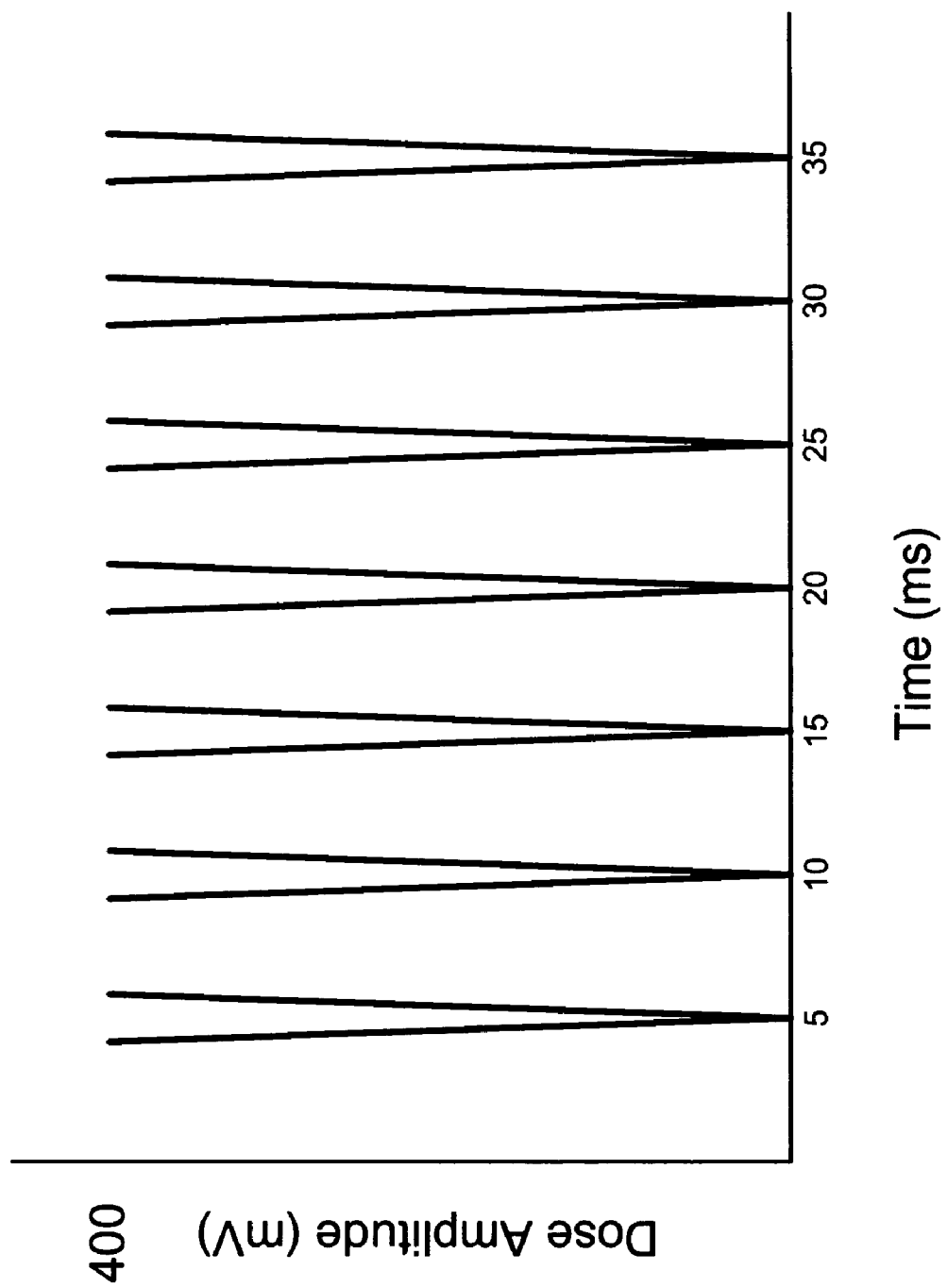
FIG. 6 is a graph of dose vs. time associated with an electron beam generated according to some embodiments.

FIG. 6 illustrates a dose provided by the first electron beam according to some embodiments using the aforementioned parameter values. As shown, the dose remains fairly predictable throughout the illustrated seven separate generations of the first electron beam. Such predictability may provide efficient imaging using particle accelerators.

The image acquired at step 64 may be used to verify that a position of the patient corresponds to a position required by the treatment plan. Such verification may be performed by processor 203 and/or by any suitable system that is or becomes known. The patient may be repositioned and flow may return to step 61 if it is determined that the position of the patient does not correspond to the position required by the treatment plan.

Returning to process steps 60, particle source 101 is controlled via trigger control 104 and injector 103 to generate a second electron current at 66. The second electron current is greater than the first electron current and may be suitable for radiation treatment. RF power source is then controlled at 67 via trigger control 104 to generate second RF power at a second pulse rate, which is less than the first pulse rate. The trigger signals, injector pulses, second electron current, second RF power and second pulse rate associated with steps 66 and 67 may be specified by program code, soft pots, or other elements of system 1.

In some embodiments using the above parameter values for the first electron current and the first pulse rate, the second electron current and second pulse rate may be 1200 mA and 30 pulses per second. Moreover, the second RF power may be 2.5 MW according to some of these embodiments.

The second electron beam is generated at step 68 based on the second injector current and the second RF power. Generation of the second electron beam may proceed according to the foregoing description of the upper three waveforms of FIG. 4. However, the time period represented by each active pulse of FIG. 4 is greater during the generation of the second electron beam than during the generation of the first electron beam.

Figure 7:
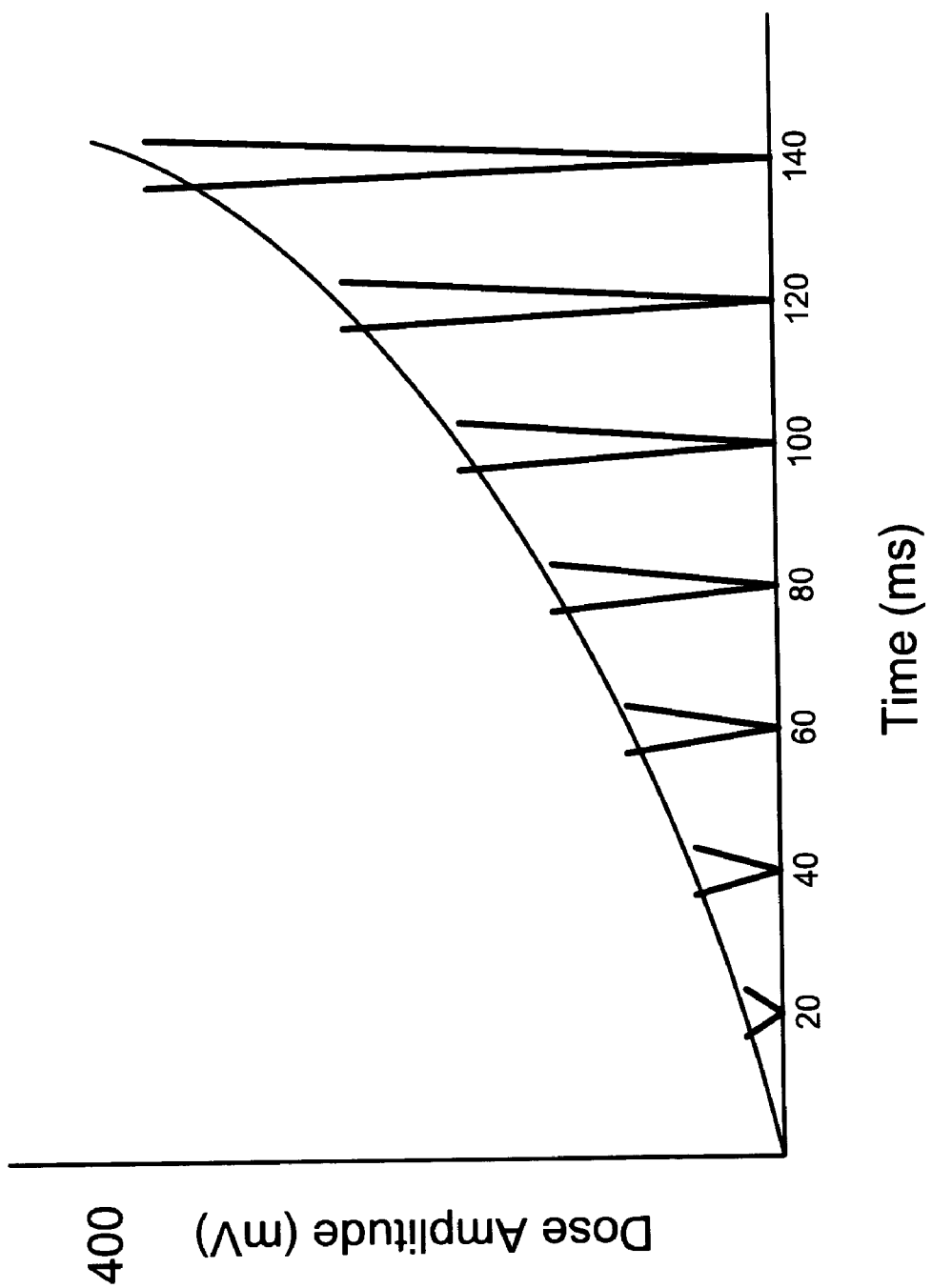
FIG. 7 is a graph of dose vs. time associated with an electron beam generated according to some embodiments.

FIG. 7 illustrates a dose provided by the second electron beam according to some embodiments using the above parameter values. As mentioned in the Background, beam loading and thermal deformation of the accelerator waveguide cause the dose to be unstable and non-linear during the formation of the second electron beam, rendering the second electron beam less suitable for imaging than the first electron beam.

At step 69, treatment radiation is delivered according to the treatment plan using the second electron beam. Such delivery may proceed according to any techniques for delivering treatment radiation that are or become known.

Some embodiments of process steps 60 include selecting electrons of the second electron beam that have a second selected energy prior to delivery of the treatment radiation at step 69. The electrons may be selected by controlling bending envelope 109 as mentioned above.

Figure 8:
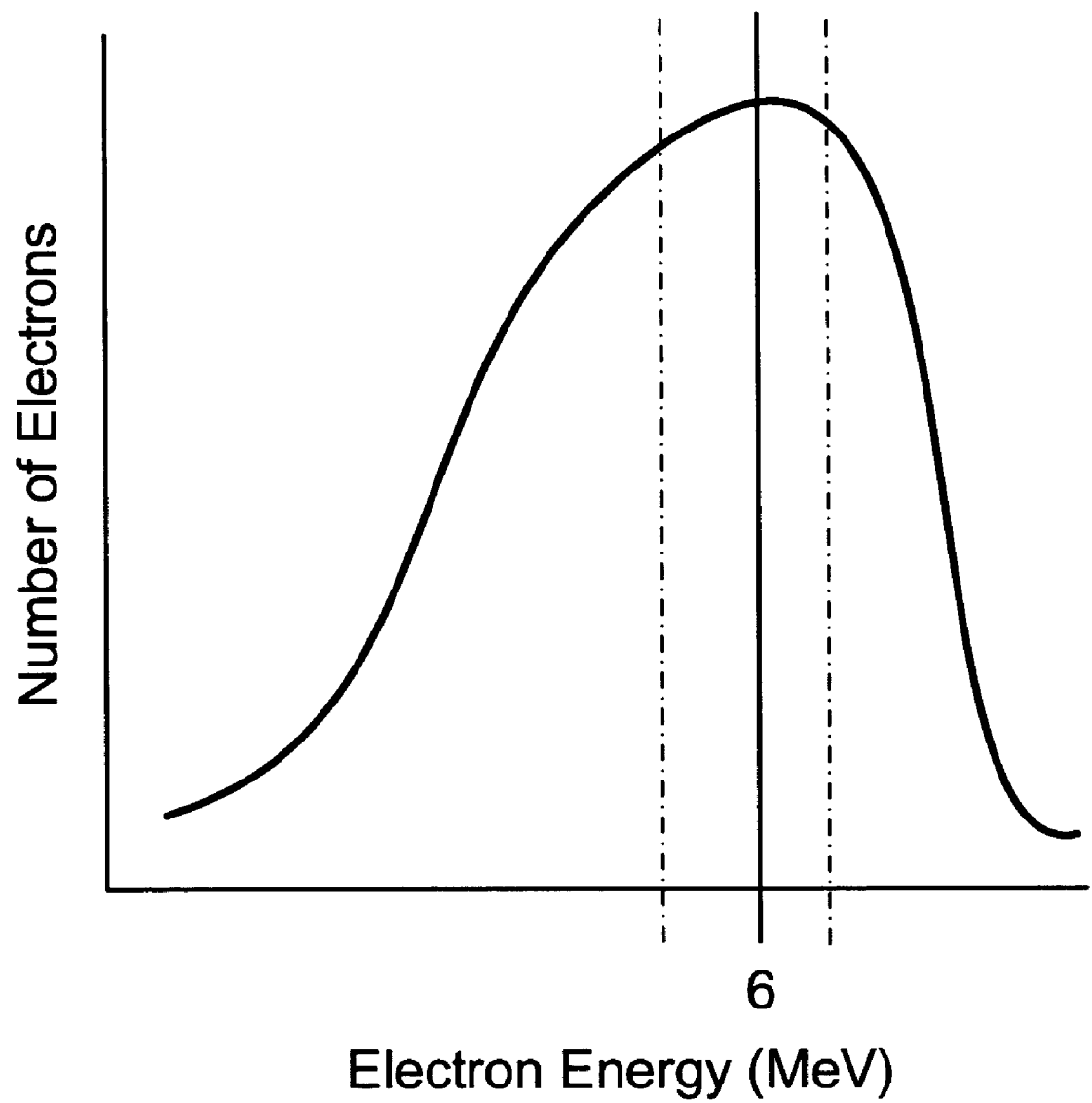
FIG. 8 is a graph of an energy spectrum associated with an electron beam generated according to some embodiments.

FIG. 8 illustrates an energy spectrum of the second electron beam according to some embodiments. The energy spectrum is different from that shown in FIG. 5. The aforementioned second selected energy may be substantially identical to the first selected energy. Accordingly, FIG. 8 shows a selected electron energy of 6 MeV, which results in the emission of electrons having energies falling between the dashed lines. The energy spectrum bounded by the dashed lines and the distribution of electrons in the energy spectrum bounded by the dashed lines is different from those of FIG. 5. These characteristics may be more suited to treatment radiation than the corresponding characteristics illustrated in FIG. 5.

The several embodiments described herein are solely for the purpose of illustration. Therefore, persons in the art will recognize from this description that other embodiments may be practiced with various modifications and alterations.

What is claimed is:

1. An apparatus comprising:
   a particle source to generate a first injector current and a second injector current, the first injector current being less than the second injector current;
   an RF power source to generate first RF power at a first pulse rate and second RF power at a second pulse rate, the first pulse rate being greater than the second pulse rate;
   an accelerator waveguide to accelerate a first electron beam based on the first injector current and the first RF power and to accelerate a second electron beam based on the second injector current and the second RF power; and
   an imaging device to acquire an image based on the first electron beam,
   wherein the second electron beam is used to deliver treatment radiation to a patient.

2. The apparatus according to claim 1, further comprising:
   an injector to control the particle source to generate the first injector current and the second injector current.

3. The apparatus according to claim 1, wherein the first RF power is less than the second RF power.

4. The apparatus according to claim 1, further comprising:
   a bending envelope to select electrons of the first electron beam having a first selected energy, and to select electrons of the second electron beam having a second selected energy,
   wherein the first selected energy is substantially equal to the second selected energy.

5. The apparatus according to claim 4, wherein an energy spectrum of the selected electrons of the first electron beam is different from an energy spectrum of the selected electrons of the second electron beam.

6. The apparatus according to claim 1, the imaging device to acquire the image at a first projection angle, and to acquire a second image based on the first electron beam at a second projection angle.

7. The apparatus according to claim 6, further comprising:
   a processor to generate a three-dimensional image based on the image and the second image.

8. The apparatus according to claim 1, further comprising:
   a processor to verify a position of the patient based on the image prior to delivery of the treatment radiation.

* * * * *